United States Patent
Swanson et al.

(10) Patent No.: US 6,454,766 B1
(45) Date of Patent: Sep. 24, 2002

(54) MICROPOROUS ELECTRODE STRUCTURE AND METHOD OF MAKING THE SAME

(75) Inventors: David K. Swanson, Campbell; Huy D. Phan, San Jose; Anant V. Hegde, Newark, all of CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/565,710

(22) Filed: May 5, 2000

(51) Int. Cl.[7] .................................................. A61B 18/18
(52) U.S. Cl. .............................. 606/41; 606/45; 606/49
(58) Field of Search ........................ 606/41–50; 607/96, 607/98, 99, 101, 116, 122, 104, 105; 604/96.01, 97.01, 99.01, 103.01

(56) References Cited

U.S. PATENT DOCUMENTS

| | | | |
|---|---|---|---|
| 4,946,440 A | * | 8/1990 | Hall ............................ 600/569 |
| 5,471,982 A | | 12/1995 | Edwards et al. |
| 5,499,971 A | | 3/1996 | Shapland et al. |
| 5,575,810 A | | 11/1996 | Swanson et al. |
| 5,836,874 A | | 11/1998 | Swanson et al. |
| 5,846,239 A | | 12/1998 | Swanson et al. |
| 5,925,038 A | | 7/1999 | Panescu et al. |
| 6,012,457 A | | 1/2000 | Lesh |
| 6,024,740 A | | 2/2000 | Lesh et al. |
| 6,099,526 A | * | 8/2000 | Whayne et al. ............. 600/374 |
| 6,251,109 B1 | * | 6/2001 | Hassett et al. ................ 606/45 |
| 6,305,378 B1 | * | 10/2001 | Lesh .......................... 128/898 |

* cited by examiner

Primary Examiner—Roy D. Gibson
(74) Attorney, Agent, or Firm—Lyon & Lyon LLP

(57) ABSTRACT

An electrode assembly adapted to transmit electrical energy for ablating body tissue includes an expandable and collapsible non-compliant body made of a durable material and defining an interior adapted to receive a medium containing ions. The body includes a porous region, an electrode adapted to transmit electrical energy located in the interior of the body, a microporous membrane located on the porous region of the non-compliant body, and the microporous membrane is sized to pass ions contained in the medium without substantial medium perfusion therethrough, to thereby enable ionic transport of electrical energy from the ion-containing medium to the exterior of the electrode assembly to ablate body tissue.

21 Claims, 6 Drawing Sheets

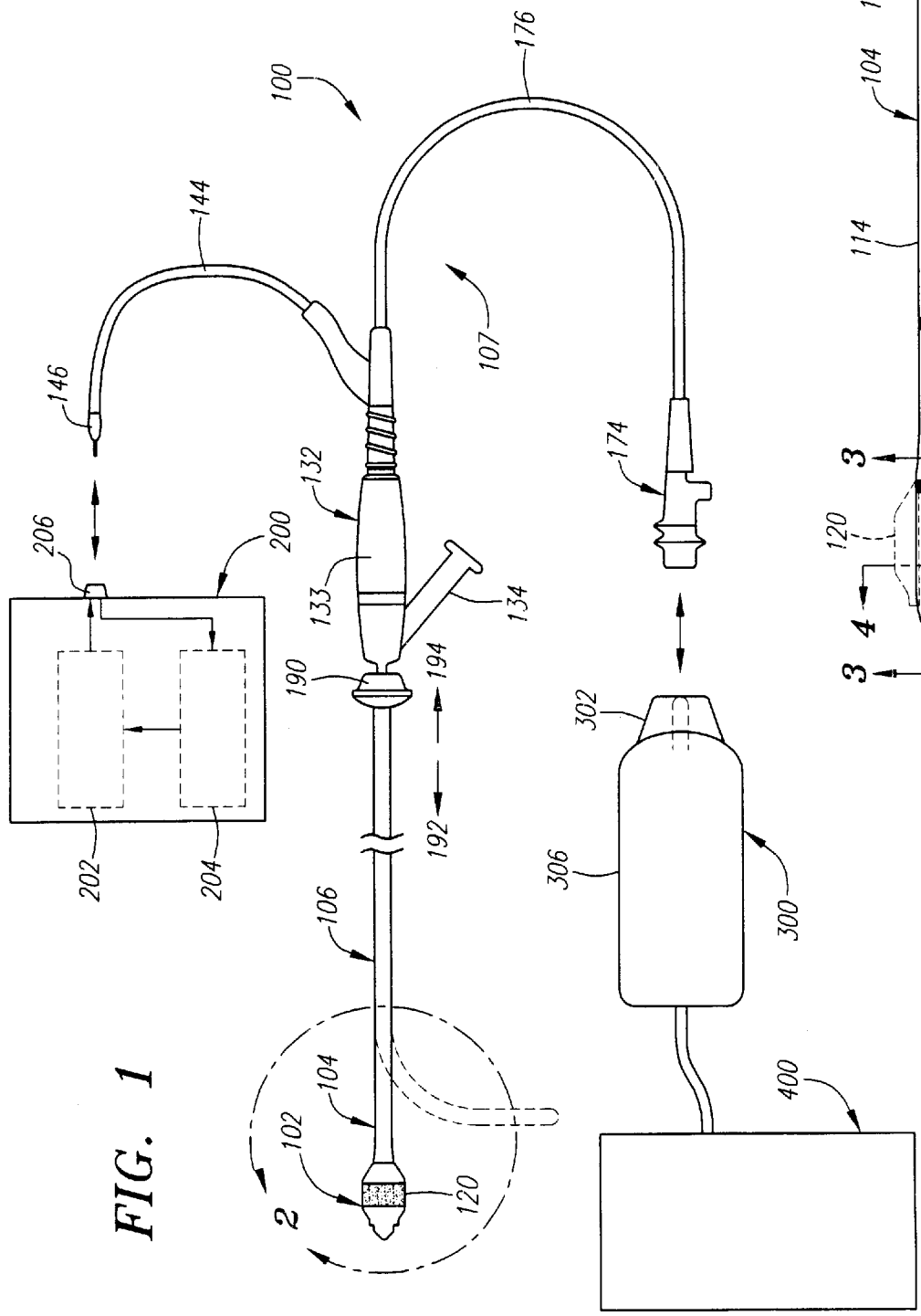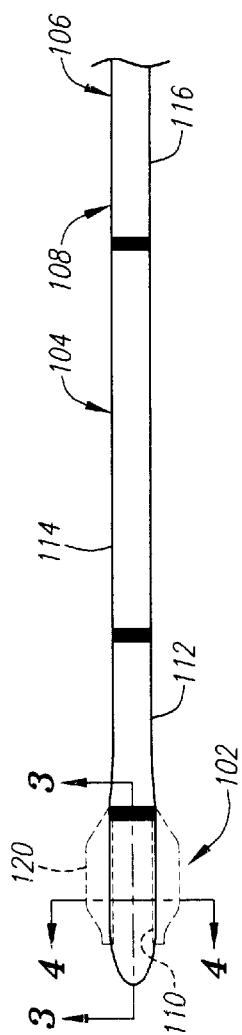
FIG. 1
FIG. 2

FIG. 9
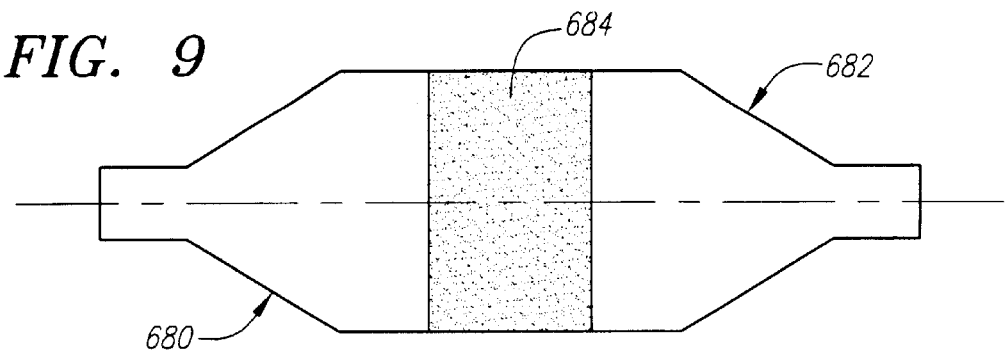
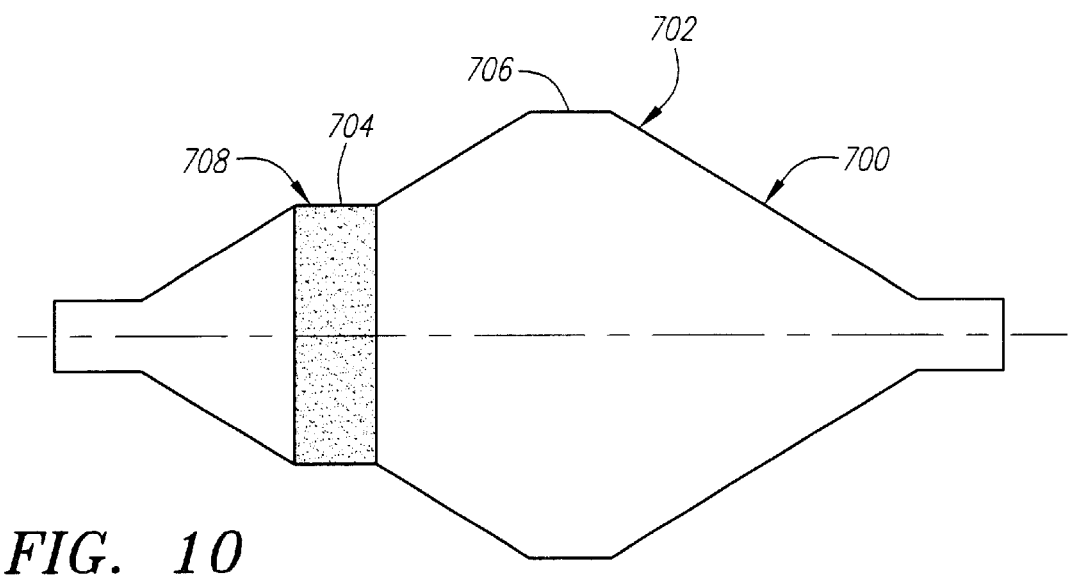
FIG. 10
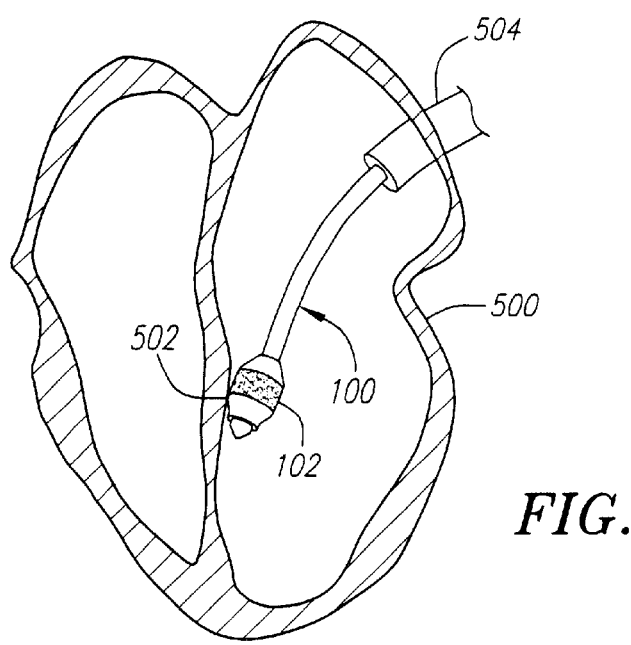
FIG. 11

MICROPOROUS ELECTRODE STRUCTURE AND METHOD OF MAKING THE SAME

FIELD OF THE INVENTION

The present invention relates to electrode body structures for ablating interior regions of the human body and manufacturing methods of making the same.

BACKGROUND OF THE INVENTION

Physicians make use of catheters today in medical procedures to gain access into interior regions of the body for ablating targeted tissue areas. These procedures, called electrophysiological therapy, are becoming more widespread for treating cardiac rhythm disturbances. It is important for the physician to control carefully and precisely these ablation procedures, especially during procedures that ablate tissue within the heart. During electrophysiological therapy, the physician introduces an ablation catheter through a main vein or artery, typically the femoral vein or artery, into the interior region of the heart that is to be treated. Placement of the ablation catheter within the heart is typically facilitated with the aid of a guide sheath. The physician then further manipulates a steering mechanism to place an ablation electrode carried on the distal tip of the ablation catheter into direct contact with the tissue that is to be ablated. The physician directs radio frequency energy from the ablation electrode through tissue to an indifferent electrode, or another catheter-mounted electrode, to ablate the tissue and form a lesion.

It has been determined that an expandable and collapsible electrode structure is advantageous for ablation of body tissue within a patient's body. The electrode structure is maintained in a collapsed condition, i.e., in a low-profile condition, when inserting the catheter into and maneuvering the catheter through the vasculature of a patient. When the electrode structure reaches the target ablation sight, the electrode structure is expanded, i.e., in a large-profile condition. The expanded electrode structure allows larger and deeper lesions to be created in the body tissue. Alternatively, the expanded electrode structure allows vascular structures such as pulmonary veins to be electrically isolated from adjacent body tissue. In one implementation of an expandable and collapsible electrode structure, it has been proposed to manufacture the electrode structure out of a microporous material. An electrically conductive element is located within the interior of the electrode structure. In use, after the electrode structure is located at the target ablation sight, a medium containing ions is introduced into the interior of the electrode structure, causing the electrode structure to expand. High frequency RF energy is transmitted through the electrically conductive element and medium containing ions, to the body tissue for ablation of such tissue. Microporous electrode structures designed to automatically, consistently and easily fold upon itself when deflated can be introduced into the body through small introducing sheaths. Previous versions of the microporous electrode bodies collapsed into a somewhat larger profile and required a larger introducer for introduction into a vein or artery.

SUMMARY OF THE INVENTION

The present invention improves the functionality of microporous electrode structures used as active elements in RF ablation catheters.

In accordance with a first aspect of the present invention, an electrode assembly adapted to transmit electrical energy for ablating body tissue includes an expandable and collapsible non-compliant body made of a durable material and defining an interior adapted to receive a medium containing ions, the body including a porous region, an electrode adapted to transmit electrical energy located in the interior of the body, a microporous membrane located on the porous region of the non-compliant body, the microporous membrane sized to pass ions contained in the medium without substantial medium perfusion therethrough, to thereby enable ionic transport of electrical energy from the ion-containing medium to the exterior of the electrode assembly to ablate body tissue.

Implementations of the first aspect of the invention may include one or more of the following. The non-compliant body is made of a material from the group consisting of Nylon, PET, PeBax, IEBA and any of the polymers used in making an angioplasty balloon. The membrane is made of a material from the group consisting of regenerated cellulose, nylon, nylon 6, nylon 6/6, polycarbonate, poly(vinylidene fluoride), a poly(vinylidene fluoride) and poly(N-vinylpyrrolidone) combination, polyethersulfone, modified acylic copolymers, and cellulose acetate. The porous region of the non-compliant body includes pores having a pore size in the range of 5 to 1,000 microns. The microporous membrane includes pores having a pore size in the range of 0.001 to 0.100 microns. The non-compliant body includes an exterior surface and the microporous membrane is located on the exterior surface of the body. The non-compliant body includes an interior surface and the microporous membrane is located on the interior surface of the body.

A second aspect of the invention involves a method of manufacturing an electrode assembly adapted to transmit electrical energy for ablating body tissue. The method includes providing an expandable and collapsible non-compliant body made of a durable material and defining an interior adapted to receive a medium containing ions, the body including a porous region; providing an electrode adapted to transmit electrical energy in the interior in the body; and attaching a microporous membrane onto porous region of the non-compliant body, the microporous membrane sized to pass ions contained in the medium without substantial medium perfusion therethrough, to thereby enable ionic transport of electrical energy from the ion-containing medium to the exterior of the electrode assembly to ablate body tissue.

Implementations of the second aspect of the invention may include one or more of the following. The body has an exterior surface, and method further includes attaching the microporous membrane to the exterior surface. The body has an interior surface, and method further includes attaching the microporous membrane to the interior surface. The microporous membrane is attached to the body with a process selected from the group consisting of adhesive bonding and heat bonding. The non-compliant body is made of a material from the group consisting of Nylon, PET, IEBA or other materials used in angioplasty balloons. The membrane is made of a material from the group consisting of regenerated cellulose, nylon, nylon 6, nylon 6/6, polycarbonate, poly(vinylidene fluoride), a poly(vinylidene fluoride) and poly(N-vinylpyrrolidone) combination, polyethersulfone, modified acylic copolymers, and cellulose acetate. The porous region of the non-compliant body includes pores having a pore size in the range of 5 to 1,000 microns. The microporous membrane includes pores having a pore size in the range of 0.001 to 0.100 microns.

A third aspect of the invention involves an electrode assembly adapted to transmit electrical energy for ablating body tissue including an expandable and collapsible non-compliant body made of a durable material and defining an interior adapted to receive a medium containing ions, the body including a porous region having a plurality of pores, an electrode adapted to transmit electrical energy located in the interior of the body, a microporous coating located on the porous region of the non-compliant body and including microporous plugs located in the pores of the porous region, the microporous coating sized to pass ions contained in the medium without substantial medium perfusion therethrough, to thereby enable ionic transport of electrical energy from the ion-containing medium to the exterior of the electrode assembly to ablate body tissue.

Implementations of the third aspect of the invention may include one or more of the following. The non-compliant body is made of a material from the group consisting of Nylon, PET, IEBA, and other polymers used to make angioplasty balloons. The membrane is made of a material from the group consisting of regenerated cellulose, nylon, nylon 6, Nylon 6/6, polycarbonate, poly(vinylidene fluoride), a poly(vinylidene fluoride) and poly(N-vinylpyrrolidone) combination, polyethersulfone, modified acylic copolymers, and cellulose acetate. The porous region of the non-compliant body includes pores having a pore size in the range of 5 to 1,000 microns. The microporous coating includes pores having a pore size in the range of 0.001 to 0.100 microns.

A fourth aspect of the invention involves a method of manufacturing an electrode assembly adapted to transmit electrical energy for ablating body tissue. The method includes providing an expandable and collapsible non-compliant body made of a durable material and defining an interior adapted to receive a medium containing ions, the body including a porous region having a plurality of pores; providing an electrode adapted to transmit electrical energy in the interior in the body; providing a microporous coating on the porous region of the non-compliant body, the microporous coating including microporous plugs located in the pores of the non-compliant body, the microporous coating sized to pass ions contained in the medium without substantial medium perfusion therethrough, to thereby enable ionic transport of electrical energy from the ion-containing medium to the exterior of the electrode assembly to ablate body tissue.

Implementations of the fourth aspect of the invention may include one or more of the following. The step of providing the microporous coating includes dipping the porous region of the non-compliant body into a viscose solution and regenerating the viscose. The non-compliant body is made of a material from the group consisting of Nylon, PET, IEBA, and other polymers used to make angioplasty balloons. The coating is made of a material from the group consisting of regenerated cellulose, nylon, nylon 6, nylon 6/6, polycarbonate, poly(vinylidene fluoride), a poly(vinylidene fluoride) and poly(N-vinylpyrrolidone) combination, polyethersulfone, modified acylic copolymers, and cellulose acetate. The pores of the porous region of the non-compliant body have a pore size in the range of 5 to 1,000 microns. The microporous coating includes pores having a pore size in the range of 0.001 to 0.100 microns.

A fifth aspect of the invention includes an electrode assembly adapted to transmit electrical energy for ablating body tissue including an expandable and collapsible electrode body including a pair of non-compliant body ends and a microporous intermediate section joining the ends, the ends and intermediate section defining an interior adapted to receive a medium containing ions, an electrode adapted to transmit electrical energy located in the interior of the body, and the microporous intermediate section sized to pass ions contained in the medium without substantial medium perfusion therethrough, to thereby enable ionic transport of electrical energy from the ion-containing medium to the exterior of the electrode assembly to ablate body tissue.

Implementations of the fifth aspect of the invention may include one or more of the following. The non-compliant body ends are made of a material from the group consisting of Nylon, PET, IEBA, and other polymers used to make angioplasty balloons. The non-compliant body ends are angioplasty balloon ends. The microporous intermediate section is made of a material from the group consisting of regenerated cellulose, nylon, nylon 6, nylon 6/6, polycarbonate, poly(vinylidene fluoride), a poly(vinylidene fluoride) and poly(N-vinylpyrrolidone) combination, polyethersulfone, modified acylic copolymers, and cellulose acetate. The microporous intermediate section includes pores having a pore size in the range of 0.001 to 0.100 microns. The body ends are substantially funnel-shaped and the microporous intermediate section is substantially tubular.

A sixth aspect of the invention involves a method of manufacturing an electrode assembly adapted to transmit electrical energy for ablating body tissue. The method includes providing an expandable and collapsible non-compliant body made of a durable material; removing an intermediate section of the non-compliant body so as to form a pair of opposite non-compliant body ends; replacing the intermediate section of the non-compliant body with a microporous intermediate section; attaching the non-compliant body ends and the microporous intermediate section so that the ends and intermediate section define an interior adapted to receive a medium containing ions, the microporous intermediate section sized to pass ions contained in the medium without substantial medium perfusion therethrough, to thereby enable ionic transport of electrical energy from the ion-containing medium to the exterior of the electrode assembly to ablate body tissue; providing an electrode adapted to transmit electrical energy in the interior in the body.

Implementations of the sixth aspect of the invention may include one or more of the following. The non-compliant body ends are made of a material from the group consisting of Nylon, PET, IEBA, and other polymers used to make angioplasty balloons. The microporous intermediate section is made of a material from the group consisting of regenerated cellulose, nylon, nylon 6, nylon 6/6, polycarbonate, poly(vinylidene fluoride), a poly(vinylidene fluoride) and poly(N-vinylpyrrolidone) combination, polyethersulfone, modified acylic copolymers, and cellulose acetate. The microporous intermediate section includes pores having a pore size in the range of 0.001 to 0.100 microns. The body ends are substantially funnel-shaped and the microporous intermediate section is substantially tubular.

A seventh aspect of the invention involves a method of manufacturing an electrode assembly adapted to transmit electrical energy for ablating body tissue. The method includes providing an expandable and collapsible non-compliant body made of a durable material and defining an interior adapted to receive a medium containing ions, the body including a porous region having a plurality of pores; providing an electrode adapted to transmit electrical energy in the interior in the body; providing a microporous coating on the porous region of the non-compliant body, the microporous coating including microporous plugs located in the pores of the non-compliant body, the microporous coating sized to pass ions contained in the medium without substantial medium perfusion therethrough, to thereby enable ionic transport of electrical energy from the ion-containing medium to the exterior of the electrode assembly to ablate body tissue.

An eighth aspect of the invention includes a method of manufacturing an electrode assembly adapted to transmit electrical energy for ablating body tissue. The method includes providing an expandable and collapsible non-compliant body made of a durable material and defining an interior adapted to receive a medium containing ions; providing an electrode adapted to transmit electrical energy in the interior in the body; creating numerous micropores in the non-compliant body, the micropores sized to pass ions contained in the medium without substantial medium perfusion therethrough, to thereby enable ionic transport of electrical energy from the ion-containing medium to the exterior of the electrode assembly to ablate body tissue.

Implementations of the eighth aspect of the invention may include one or more of the following. The micropores are created using an ion-beam process. The micropores are located only in a central section of the body. The non-compliant body is made of a material from the group consisting of Nylon, PET, IEBA, and other polymers used to make angioplasty balloons. The non-compliant body is an angioplasty balloon. The micropores have a pore size in the range of 0.001 to 0.100 microns.

A ninth aspect of the invention involves an electrode assembly adapted to transmit electrical energy for ablating body tissue including an expandable and collapsible non-compliant body made of a durable material and defining an interior adapted to receive a medium containing ions, the body having a step-shaped configuration formed by a first-diameter portion and a second-diameter portion with a diameter greater than the first-diameter portion, an electrode adapted to transmit electrical energy located in the interior of the body, a microporous structure located in the first-diameter portion of the non-compliant body, the microporous structure sized to pass ions contained in the medium without substantial medium perfusion therethrough, to thereby enable ionic transport of electrical energy from the ion-containing medium to the exterior of the electrode assembly to ablate body tissue.

Implementations of the ninth aspect of the invention may include one or more of the following. The first diameter portion of the body includes a porous region and the microporous structure includes a microporous membrane adhered to the porous region of the body. The body includes an inside surface and the microporous membrane is adhered to the inside surface of the body. The body includes an outside surface and the microporous membrane is adhered to the outside surface of the body. The first diameter portion of the body includes a porous region having a plurality of pores, the microporous structure includes a microporous coating adhered to the porous region of the body, and the microporous coating includes microporous plugs located in the pores of the porous region of the body.

A tenth aspect of the invention involves a method of manufacturing an electrode assembly adapted to transmit electrical energy for ablating body tissue. The method includes providing an expandable and collapsible non-compliant body made of a durable material and defining an interior adapted to receive a medium containing ions, the body having a step-shaped configuration formed by a first-diameter portion and a second-diameter portion with a diameter greater than the first-diameter portion; providing an electrode adapted to transmit electrical energy in the interior in the body; providing a microporous structure in the first-diameter portion of the non-compliant body, the microporous structure sized to pass ions contained in the medium without substantial medium perfusion therethrough, to thereby enable ionic transport of electrical energy from the ion-containing medium to the exterior of the electrode assembly to ablate body tissue.

Implementations of the tenth aspect of the invention may include one or more of the following. The first diameter portion of the body includes a porous region, the microporous structure includes a microporous membrane, and the step of providing a microporous structure in the first-diameter portion of the non-compliant body includes adhering the microporous membrane to the porous region of the body. The body includes an inside surface and the microporous membrane is adhered to the inside surface of the body. The body includes an outside surface and the microporous membrane is adhered to the outside surface of the body. The first diameter portion of the body includes a porous region having a plurality of pores, the microporous structure includes a microporous coating, and the step of providing a microporous structure in the first-diameter portion of the non-compliant body includes dipping the porous region of the body in a viscose solution and regenerating the viscose. The step of providing a microporous structure in the first-diameter portion of the non-compliant body includes creating a plurality of micropores in the first-diameter portion using an ion-beam process.

Other and further objects, features, aspects, and advantages of the present inventions will become better understood with the following detailed description of the accompanying drawings.

BRIEF DESCRIPTION OF DRAWINGS

The drawings illustrate both the design and utility of preferred embodiments of the present invention, in which:

FIG. 1 is a schematic illustration of an RF ablation catheter system including an electrode structure constructed in accordance with an embodiment of the present invention;

FIG. 2 is partial side-elevational view of the catheter of FIG. 1, particularly showing the operative distal region, deflectable region, and main region of the catheter;

FIG. 9 is a side-elevational view of a microporous electrode structure constructed in accordance with an additional embodiment of the invention;

FIG. 10 is a side-elevational view of a microporous electrode structure constructed in accordance with a further embodiment of the invention; and FIG. 11 is a cross-sectional view of the heart with an embodiment of the catheter shown therein.

DETAILED DESCRIPTION OF THE DRAWINGS

Figure 3:
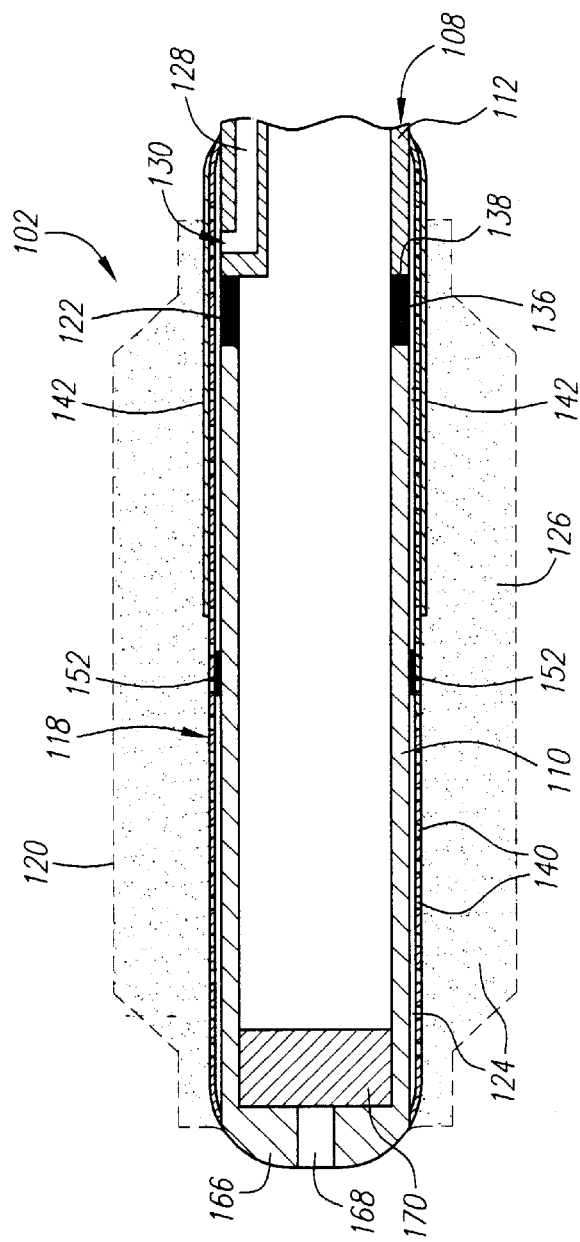
FIG. 3 is a longitudinal cross-sectional view of the operative distal region of the catheter, taken along line 3—3 of FIG. 2.

With reference to FIG. 1, a RF ablation catheter 100 including a microporous electrode body 120 constructed in accordance with a preferred embodiment of the present invention will now be described. To assist the reader in gaining a better understanding of the invention, the catheter 100 and a number of catheter-related instruments will be described before a description of the microporous electrode structure of the present invention. The catheter 100 may be connected to a RF generator 200 such as that described in Jackson et al., U.S. Pat. No. 5,383,874, the specification of which is fully and expressly incorporated herein by reference. The RF generator 200 provides the catheter 100 with a source of RF ablation energy. Thus, when operated, the RF generator 200 allows the physician to ablate tissue such as heart tissue in a controlled manner, resulting in a tissue lesion with the desired characteristics. The catheter 100 may also be connected to a motor drive unit 300 and an ultrasonic (or other imaging) signal processor 400, which when operated, allows the physician to obtain images of the target tissue site, preferably during and subsequent to the ablation process.

The catheter 100 can be functionally divided into four regions: the operative distal catheter region 102, a deflectable catheter region 104, a main catheter region 106, and an interfacing proximal catheter region 107. The microporous electrode body 120 of the distal catheter region 102 represents the active component that provides the ablative capability to the catheter 100. The deflectable catheter region 104 provides steering capability to the catheter 100, and particularly, provides an efficient and effective means for manipulating the distal catheter region 102. The main catheter region 106 provides the catheter 100 with the required length to deliver the distal catheter region 102 from the insertion point of the patient (typically, the femoral vein or artery) to the targeted tissue site. Lastly, the proximal catheter region 107, which includes a handle assembly 132 and a proximal adapter 174, provides interfacing capability between the catheter 100 and other instruments such as the RF generator 200, motor drive unit 300, and signal processor 400, as well as a means for introducing and removing fluids into and out of the catheter 100.

With reference to FIG. 2, the catheter 100 includes a catheter body 108 that carries a differing number of functional lumens and may have varying flexibility along its length. In this regard, the catheter body 108 is composed of several extruded tubular elements affixed together in an axial arrangement. In particular, the catheter body 108 may include first and second tubular elements 110, 112, which form, in conjunction, the structure of the distal catheter region 102; a third tubular element 114, which forms the structure of the deflectable catheter region 104; and a fourth tubular element 116, which forms the structure of the main catheter region 106. It should be noted, however, that the catheter body 108 may include any number of tubular elements required to provide the desired functionality to the catheter 100.

The tubular elements 110, 112, 114, and 116 may be composed of a flexible and biocompatible material. In the illustrated embodiment, the second, third, and fourth tubular elements 112, 114, and 116 may be composed of a non-conductive thermoplastic elastomer such as polyurethane. Preferably, if ultrasound imaging is used, the first tubular element 110 is composed of a more ultrasound transparent material such as polyethylene. The tubular elements 112, 114 and 116 are suitably bonded together by means such as adhesive or thermal bonding to integrally form the catheter body 108. Additionally, heat shrink tubing (not shown) can be shrunk over the catheter body 108 to provide a more integral catheter structure. The catheter body 108 can be variously sized, assuming the selected size allows the catheter body 108 to be routed through the vasculature of the patient to the targeted tissue site. By way of a non-limiting example, a 9F catheter body 108 having a length of 100 cm will allow the catheter distal region 102 to be delivered to the interior of the heart via the femoral vein or artery.

Figure 4:
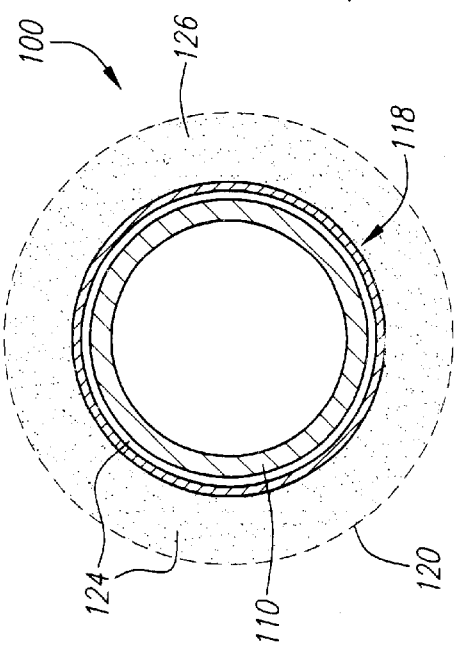
FIG. 4 is a cross-sectional view of the operative distal region of the catheter, taken along line 4—4 of FIG. 2.

With reference to FIGS. 3 and 4, the catheter distal region 102 will now be described in detail. The catheter distal region 102 carries an ablation assembly 118, which includes the expandable-collapsible electrode body or structure 120 and an actuating electrode, and particularly, an electrode ring 122. The electrode body 120 is suitably mounted to the catheter body 108 such that an interior region 124 of the electrode body 120 is in communication with substantially the entire exterior surface of the first tubular element 110, and at least a portion of the exterior surface of the second tubular element 112.

The geometry of the electrode body 120 may be altered between a collapsed geometry and an enlarged, expanded geometry (represented by broken line). In the illustrated embodiment, an inflation medium 126 under pressure is used to fill the interior region 124, and thus, inflate and maintain the electrode body 120 in the expanded geometry. The inflation medium 126 is conveyed to and from the interior region 124 of the electrode body 120 via an inflation lumen 128 formed through the catheter body 108, and in particular, the second, third and fourth tubular elements 112. The inflation lumen 128 is in fluid communication with the interior region 124 of the electrode body 120 via an infusion hole 130 formed through the wall of the catheter body 108, and specifically, the wall of the second tubular element 112.

With reference further to FIG. 1, the inflation lumen 128 terminates proximally in the handle assembly 132, and particularly within a handle 133 of the handle assembly 132. The handle assembly 132 further includes an inflation port 134, which is in fluid communication with the inflation lumen 128 within the handle 133. Thus, inflation medium 126 can be introduced into, or removed from, the inflation port 128, providing a convenient means of selectively inflating and deflating the electrode body 120.

With reference back to FIGS. 3 and 4, the electrode ring 122 is located between the first tubular element 110 and the second tubular element 112. In particular, a proximal edge 136 of the first tubular element 110 and a distal edge 138 of the second tubular element 112 are affixed to the opposite edges of the electrode ring 122 by suitable means such as adhesive or thermal bonding, providing an integral connection between the first tubular element 110 and the second tubular element 112. The electrode ring 122 provides RF energy to the electrode body 120 via the inflation medium 126. In this regard, the electrode ring 122 is composed of a material having both a relatively high electrical conductivity and a relatively high thermal conductivity, e.g., stainless steel, gold, platinum, or platinum/iridium, and is in communication with the interior region 124 of the electrode body 120.

It should be noted that the ring-like structure of the electrode ring 122 provides a relatively large circumferential exterior surface of the electrode ring 122 to be in communication with the interior region 124 of the electrode body 120, providing an efficient means of energizing the inflation medium 126. Although the actuating electrode is described as a ring, the actuating electrode can take the form of any suitable structure that can be placed in contact with the inflation medium 126. The length of the electrode ring 122 can be accordingly varied to increase or decrease the amount of RF energy delivered to the inflation medium 126. The location of the electrode ring 122 can also be varied, but should be positioned such that the imaging capability of the catheter 100 is not interfered with.

The inflation medium 126 is composed of an electrically conductive liquid that establishes an electrically conductive path from the electrode ring 122 to the surface of the electrode body 120. Preferably, the electrically conductive medium 126 possesses a low resistivity to decrease ohmic losses and, thus, ohmic heating effects, within the electrode body 120. The composition of the electrically conductive medium 126 can vary. In the illustrated embodiment, the electrically conductive medium 126 comprises a hypertonic saline solution having a sodium chloride concentration at or near saturation, which is about 22% weight by volume.

Although the material that the electrode body 120 is composed of is electrically non-conductive, the electrode body 120 includes pores 140 on at least a portion of its surface. The porous structure of the electrode body 120 acts as the energy-emitting surface of the electrode body 120, establishing ionic transport of RF energy from the electrode ring 122, through the electrically conductive medium 126, through the pores 140, and into the tissue outside of the electrode body 120, thereby creating a lesion.

The geometry of the energy-emitting surface of the electrode body 120 can be customized to more efficiently produce desired lesion characteristics. In particular, the delivery of RF energy from the electrode ring 122 to the electrode body 120 can be concentrated in certain regions of the electrode body 120 by masking the pores 140 of the electrode body 120. For example, in the illustrated embodiment, a mask 142, composed of a non-porous material such as polyurethane is bonded to a portion of the electrode body 120, and particularly, the proximal region of the electrode body 120. In this manner, the RF energy delivered to the electrode body 120 is concentrated in the distal region of the electrode body 120.

The electrical resistivity of the electrode body 120 has a significant influence on the tissue lesion geometry and controllability. Ablation with a low-resistivity electrode body 120 enables more RF power to the tissue and results in deeper lesions. On the other hand, ablation with a high-resistivity electrode body 120 generates more uniform heating, therefore improving the controllability of the lesion. Generally speaking, lower resistivity values for the electrode body 120 (below about 500 ohm-cm) result in deeper lesion geometries while higher resistivity values for the electrode body 120 (above about 500 ohm-cm), result in shallower lesion geometries.

The electrical resistivity of the electrode body 120 can be controlled by specifying the pore size of the material, the porosity of the material (space on the body that does not contain material), and the water absorption characteristics (hydrophilic versus hydrophobic) of the material. In general, the greater the pore size and porosity, the lower the resistivity of the electrode body 120. In contrast, the lesser the pore size and porosity, the higher the resistivity of the electrode body 120. The size of the pores 140 is selected such that little or no liquid perfusion through the pores 140 results, assuming a maximum liquid pressure within the interior region 124 of the electrode body 120.

In general, hydrophillic materials possess a greater capacity to provide ionic transfer of radiofrequency energy without significant perfusion of liquid through the electrode body 120 than do hydrophobic materials. Additionally, hydrophilic materials generally have lower coefficients of friction with body tissues than have hydrophobic materials, facilitating routing of the catheter 100 through the vasculature of the patient. In this regard, the catheter body 108 is preferably composed of a hydrophillic material. Further details concerning the manufacture of the electrode body 120, including the specification of the pore size, porosity, and water absorption characteristics of the material, are disclosed in Swanson et al., U.S. Pat. No. 5,797,903, the specification of which is fully and expressly incorporated herein by reference.

With reference further to FIG. 1, delivery of RF energy to the ablation assembly 118 is controlled by the RF generator 200, as briefly discussed above. The RF generator 200 includes a RF source 202 for generating the RF energy and a controller 204 that controls the amplitude of and time during which the RF source 202 outputs RF energy. The RF generator 200 is electrically coupled to the ablation assembly 118 of the catheter 100 via the handle assembly 132. Specifically, the handle assembly 132 includes a cable 144 and a plug 146 associated therewith. The plug 146 mates with a socket 206, which is electrically coupled to the RF source 202 and controller 204, located on the RF generator 200.

Although not shown, ablation wires are routed through the catheter body 108 and include distal ends suitably connected to the electrode ring 122 and proximal ends suitably connected to the handle 133, in communication with the cable 144.

Thus, mating of the plug 146 with the socket 206 of the RF generator 200 provides an electrical connection between the RF source 202 and the electrode ring 122. Operation of the RF generator 200 provides RF energy to the electrode ring 122, which in turn is ionically transferred through the inflation medium 126 and out through the pores 140 of the electrode body 120, into the targeted tissue region.

With reference specifically to FIG. 3, to facilitate control of the RF energy delivery, the catheter 100 may include one or more temperature sensing elements 152 carried by the electrode body 120.

Although not shown, the catheter 100 may include an ultrasonic imaging transducer and imaging core rotatably disposed within the catheter body 108 for generating 360-degree two-dimensional ultrasonic images of the targeted tissue region. The proximal adapter 174 (FIG. 1) provides a suitable interface between the imaging core located in proximal cable 176 and the motor drive unit 300 and signal processor 400. The proximal adapter 174 mates with a hub 302 of the motor drive unit 300, which allows the motor drive unit 300 and signal processor 400 to interact with the imaging core 156.

To provide a more effective means of placing the electrode body 120 adjacent the targeted tissue region, the catheter 100 has a steering capability. A steering wire (not shown) is slidably disposed within the catheter body 108 and includes a distal end attached at one end between the second tubular element 112 and the third tubular element 114 and a proximal end suitably mounted within the handle 133. The handle assembly 132 further includes a collar 190, which moves longitudinally relative to the handle 133. The collar 190 is mounted to the proximal end of the catheter body 108, and particularly, the proximal end of the fourth tubular element 116. Distal movement of the collar 190 relative to the handle 133 (in the direction indicated by the arrow 192), causes the steering wire to move proximally relative to the catheter body 108, which, in turn, tensions the steering wire, thus pulling and bending the catheter deflectable region 104 into an arc (shown by broken lines). On the contrary, proximal movement of the collar 190 relative to the handle 133 (in the direction indicated by the arrow 194), causes the steering wire to move distally relative to the catheter body 108, which, in turn, relaxes the steering wire, thus allowing the resiliency of the third tubular element 114 to place the catheter deflectable region 104 of the catheter 100 back into a rectilinear configuration.

The present invention relates to a microporous electrode body 120 and method of making the same, and will now be described. An electrode body 120 including microporous, hydrophilic characteristics is desirable for optimal lesion creation in body tissue. Further, it is important for the microporous electrode body 120 when deflated or collapsed to have a low profile to facilitate introduction and routing of the electrode body 120 and catheter 100 through the vasculature of the patient and when inflated or expanded to have a large profile so that larger, deeper lesions can be created in the desired body tissue. To possess both of these qualities, the microporous electrode body 120 should be designed to automatically, consistently and easily fold upon itself when deflated. Microporous electrode structures designed to automatically, consistently and easily fold upon itself when deflated can be introduced into the body through small introducing sheaths. Previous versions of the microporous electrode bodies collapsed into a somewhat larger profile and required a larger introducer for introduction into a vein or artery. Microporous electrode bodies in the past exhibited low burst pressures, typically less than 2 atmospheres because of limited material strength of the microporous materials. Thus, the microporous electrode bodies were susceptible to bursting, cracking or breaking, i.e., leakage.

Figure 5A:
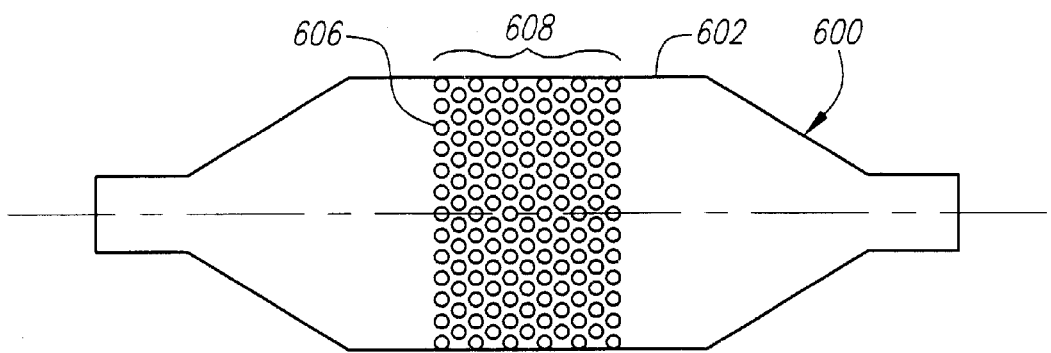
FIGS. 5A, 5B and 5C are side elevational views of an electrode body, microporous membrane, and microporous electrode structure, respectively, constructed in accordance with an embodiment of the invention.
Figure 5B:
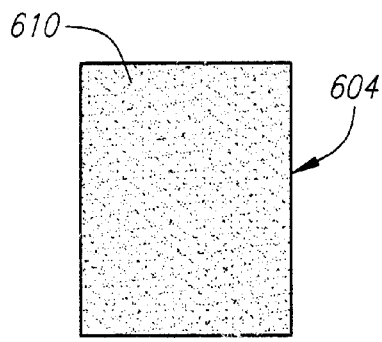
Figure 5C:
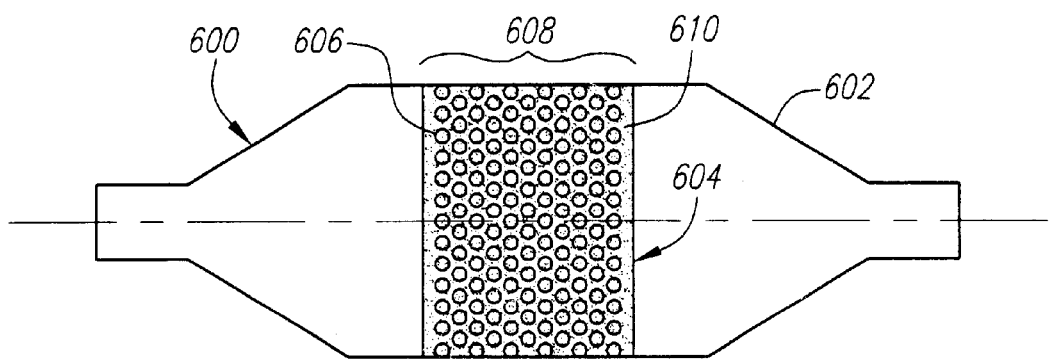

With reference to FIGS. 5A–5C, a microporous electrode body 600 constructed in accordance with an additional embodiment of the invention that overcomes the aforementioned drawbacks of microporous electrode structures in the past will now be described. Electrode body 600 includes a porous non-compliant body 602 and a microporous membrane 604. As used herein, the term "non-compliant" means that the body does not substantially stretch when inflated with fluid. The body may be inflated to a predetermined size, but does not stretch or expand beyond that size by more than about 15% when inflated above the rated inflation pressure. The non-compliant body 602 is preferably made from the same or similar materials as an angioplasty balloon. The non-compliant body 602 may be made of Nylon, PET, PEBA or similar non-compliant material by blow molding, stretch blow molding or similar process and is porous with pores, cuts or holes 606 preferably located in a central region 608 and having a pore size of 5 to 1,000 microns. As used below, "pores" refers to pores, cuts or holes. The pores 606 may be arranged in a pattern and a location customized to concentrate the delivery of RF energy in certain regions of the electrode body 600 to more efficiently produce desired lesion characteristics. Alternatively, the pores 606 may be distributed evenly throughout the body 602 and certain regions of the body 602 may be masked by a non-porous material such as polyurethane to concentrate the delivery of RF energy in certain un-masked regions of the electrode body 600. The pores 606 may be made in the body 602 using a laser or die cutting process. The purpose of these pores 606 is to provide a pathway for the ions to exit from inside the body 602 to outside of the body 602. The microporous membrane 604 is adhered to the inside of the body 602 by an adhesive bonding process using adhesives or epoxies, by a heat fusing process, or by a similar process. The microporous membrane 604 is preferably tubular and located along the central region 608 of the longitudinal length of the body 602. The membrane 604 is microporous with pores 610 that are 0.001 to 0.100 microns in size. Advantages of the above-described electrode body 600 include that the electrode body is easy to fabricate and fold because the bulk properties of the balloon are the same as angioplasty balloons, which as described above, facilitates introduction of the electrode body 600 into and through the vasculature of the patient's body.

Figure 6:
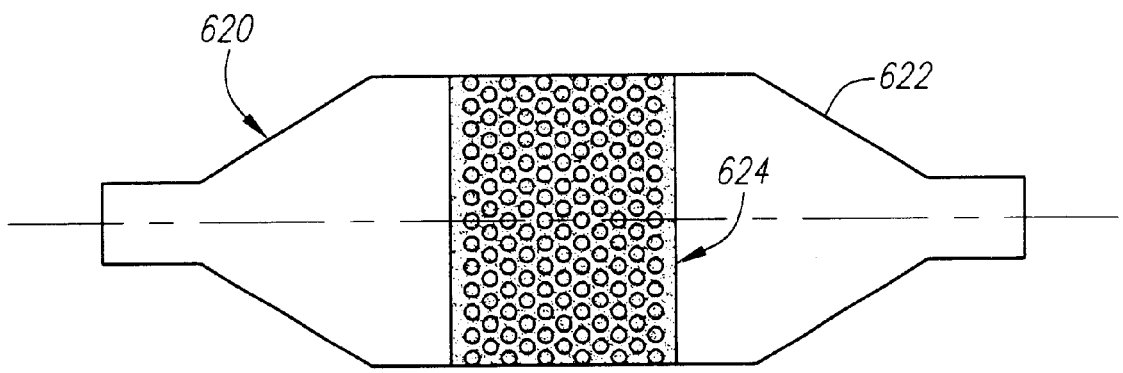
FIG. 6 is a side-elevational view of a microporous electrode structure constructed in accordance with an alternative embodiment of the invention.
Figure 7A:
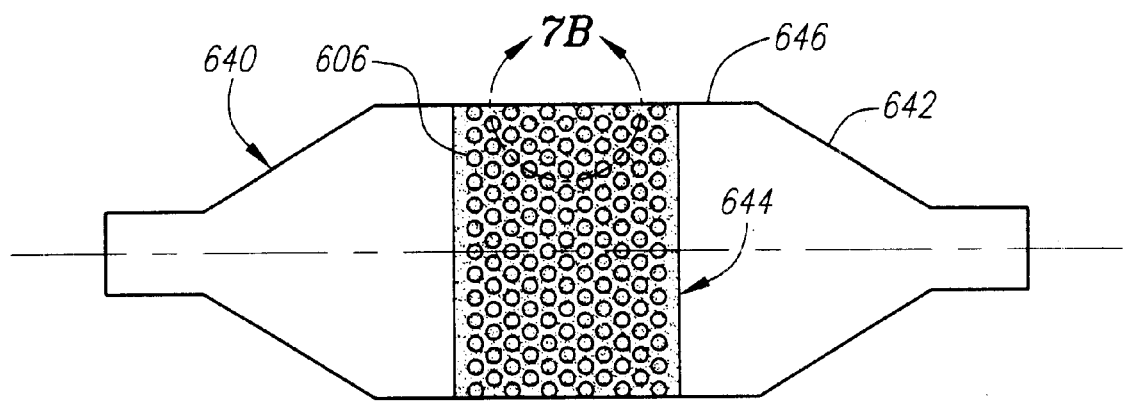
FIG. 7A is a side-elevational view of a microporous electrode structure constructed in accordance with a further embodiment of the invention.
Figure 7B:
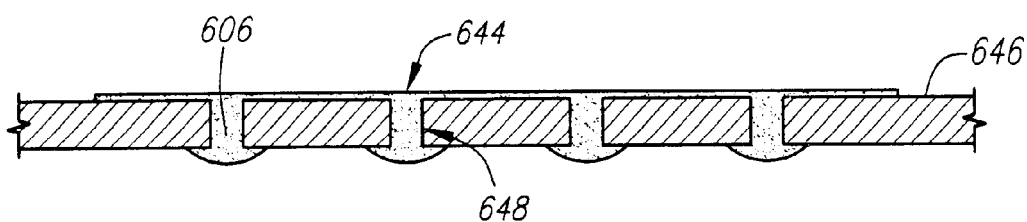
FIG. 7B is a partial cross-sectional view of the of the electrode structure and illustrates an embodiment of microporous plugs and a microporous coating on the electrode structure.

With reference to FIG. 6, a microporous electrode body 620 and method of making the same in accordance with an alternative embodiment of the invention will now be described. Electrode body 620 includes a porous non-compliant body 622 and a microporous membrane 624 that are similar in all respects to the porous non-compliant body 602 and the microporous membrane 604 described above with respect to FIGS. 5A–5C, except microporous membrane 624 is located on the outside of the non-compliant body 622 instead of the inside of the body 622. Locating the microporous membrane 624 on the outside of the body 622 is advantageous because it is easier to apply the membrane to the exterior of the body 622 during manufacturing. With reference to FIGS. 7A and 7B, a microporous electrode body 640 and method of making the same in accordance with another embodiment of the invention will now be described. Electrode body 640 includes a porous non-compliant body 642, which is similar to the body 602 described above, and a microporous layer 644 that covers a selected region of a surface 646 of the body 642 and also occupies or plugs the pores 606 in the body 642. To create the microporous layer 644, the perforated non-compliant body 642 is dipped in viscose and regenerated using mild acid. This creates the microporous layer 644 on the surface 646 and in the pores 606. Because the viscose flows into the pores 646 of the body 642, after regeneration, the extra material that passes through the pores 646 creates "rivet-like" members or plugs 648 that prevent the microporous layer 644 from separating away from the body 642. The pores 606 may be plugged with numerous microporous materials such as, without limitation, regenerated cellulose, polysulfone and hydrdogel. The pore size in the body 642 and the microporous layer 644 may be the same as that described above with respect to FIGS. 5A–5C. Similarly, the pores may be arranged in a pattern customized to concentrate the delivery of RF energy in certain regions of the electrode body 640, more efficiently producing desired lesion characteristics. Advantages of the above-described electrode body 640 include that it is easy to manufacture, the body 640 has a smooth outer surface causing less tissue trauma and less friction, and the microporous layer 644 is retained to the body 642 by the plugs 648, inhibiting the microporous layer 644 from being released into the patient's blood stream during use.

Figure 8A:
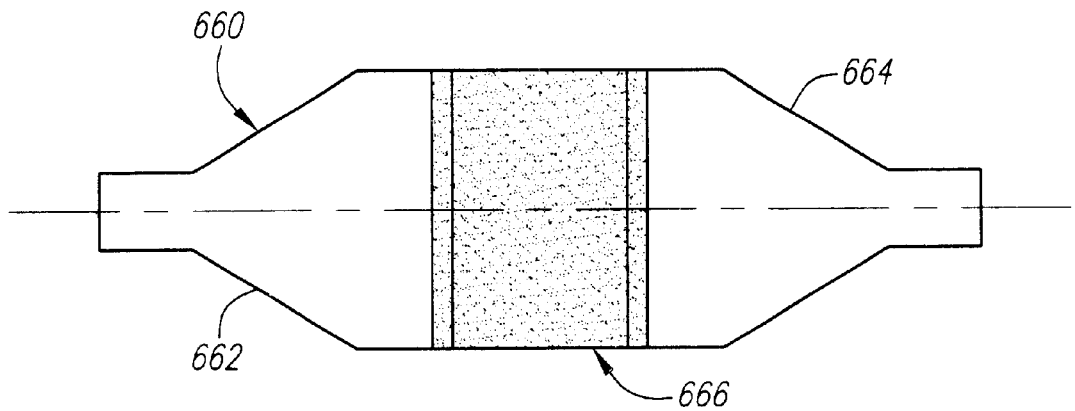
FIG. 8A is a side-elevational view of a microporous electrode structure constructed in accordance with another embodiment of the invention.
Figure 8B:
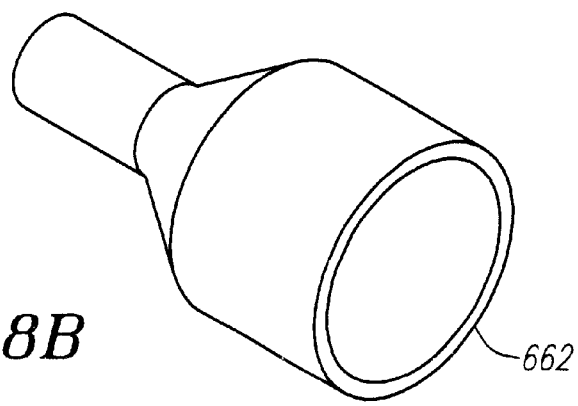
FIG. 8B is perspective view of an embodiment of a non-compliant body end.
Figure 8C:
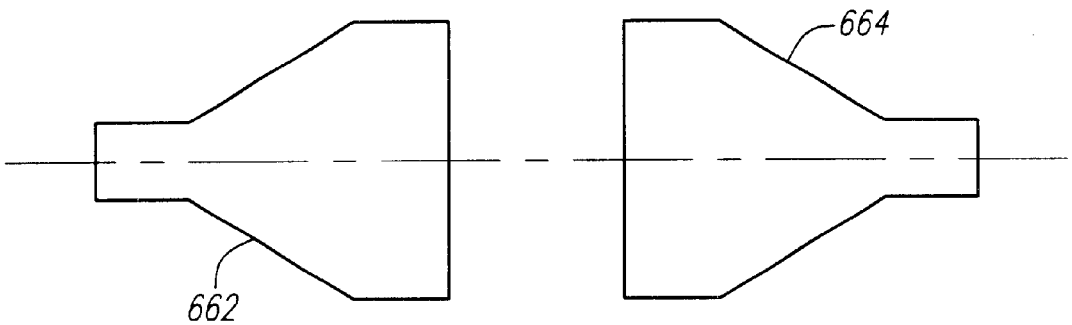
FIG. 8C is a side-elevational view of an embodiment of a pair of non-compliant body ends.

With reference to FIGS. 8A–8C, a microporous electrode body 660 and method of making the same in accordance with a further embodiment of the invention will now be described. The microporous electrode body 660 includes non-compliant body ends 662, 664 and an intermediate microporous structure 666. In a preferred embodiment, the body ends 662, 664 are "funnel-shaped" and the intermediate microporous structure 642 is tubular. The microporous electrode body 660 may be manufactured by fabricating a non-compliant body, which is similar to body 602 described above, in the desired shape of the electrode body 660 by a process such as, but not by limitation, blow molding or stretch blow molding, cutting out and removing an intermediate tubular section of the body so as to form funnel-shaped body ends 662, 664, and bonding the intermediate microporous structure 666 to the body ends 662, 664, as shown in FIG. 8A, by an adhesive bonding process, heat fusing process or similar method. The pore size in the microporous structure 666 is similar the pore size described above with respect to microporous membrane 604 of FIGS. 5A–5C. Similarly, the microporous structure 666 of the electrode body 662 may have a configuration and location other than that shown in FIG. 8A in order to concentrate the delivery of RF energy in another region or other regions of the electrode body 640. Advantages of the above-described electrode body 660 include that it is easy to manufacture, the body 660 has a low profile, and is easy to fold and re-fold, which as described above, facilitates introduction of the electrode body 660 into and through the vasculature of the patient's body.

With reference to FIG. 9, a microporous electrode body 680 and a method of making the same in accordance with a further embodiment of the invention will now be described. The microporous electrode body 680 includes a porous non-compliant body 682 that is similar to the porous non-compliant body 602 described above, except that the plurality of pores are micropores 684 having a size of 0.001 to 0.100 microns instead of 5 to 1,000 microns. The micropores 684 are created by an ion-beam process or similar process in a region of the non-compliant body 602 where energy is desired to be transmitted. Advantages of the above-described electrode body 680 include that it is easy to manufacture, the body 680 has a low profile, and is easy to fold and re-fold, which as described above, facilitates introduction of the electrode body 680 into and through the vasculature of the patient's body.

With reference to FIG. 10, a microporous electrode body 700 and a method of making the same in accordance with a further embodiment of the invention will now be described. The microporous electrode body 700 includes a non-compliant body 702 made by the same process and same material as the porous non-compliant body 602 described above, but includes a different configuration, e.g., a step-shaped configuration. The non-compliant body 702 has a first-diameter portion 704 and a second-diameter portion 706 that is larger in diameter than the first-diameter portion 704. The first-diameter portion 704 may include a microporous structure 708 having a pore size of 0.001 to 0.100 microns in size. The microporous structure 708 may include any of the microporous structures made by any of the manufacturing methods described above with respect to FIGS. 5–9. For example, the non-compliant body 702 may be porous in a region of the first-diameter portion 704 and the microporous structure 708 may include a microporous membrane adhered to an inside or outside surface of the body 702 (FIGS. 5A–5C, 6) or may include a microporous layer (FIGS. 7A, 7B). Alternatively, the microporous structure 708 may be an intermediate microporous structure attached to different sections of the non-compliant body 702 (FIG. 8). Alternatively, the microporous structure 708 may consist of a plurality of micropores 0.001 to 0.100 microns in size created in the non-compliant structure by an ion-beam process or similar process (FIG. 9). Locating the microporous structure 708 in the first-diameter portion 704 makes it easy to position the electrode body 700 at the orifice of a pulmonary vein or other blood vessel and create a circular lesion at the orifice. Other advantages of this embodiment of the invention include that it is easy to manufacture, the body 700 has a low profile, and is easy to fold and re-fold, which as described above, facilitates introduction of the electrode body 700 into and through the vasculature of the patient's body.

With reference to FIG. 11, operation of the catheter 100 to create a lesion at a targeted tissue ablation site 502 within a heart 500 will now be described. For the purposes of brevity in explanation, it is assumed that a guide sheath 504 has been previously routed (via a guide catheter or guide wire) through the patient's vasculature, and into the heart chamber, adjacent the targeted tissue ablation site 502. It is also assumed that a mapping catheter has been introduced through the guide sheath 504 and used to identify a potential ablation site as the targeted tissue ablation site 502 relative to anatomical landmarks within the heart 500. A variety of diagnostic mapping techniques can be employed to accomplish this objective. Further details concerning the use of a mapping catheter to identify potential ablation sites within the heart are set forth in Greenspon et al., U.S. Pat. No 5,954,661, the specification of which is fully and expressly incorporated herein by reference. For purposes of brevity, all associated imaging steps, e.g., ultrasonic imaging steps, for assisting the user to position the catheter distal region 102 adjacent the targeted tissue ablation site 502 will not discussed.

After the mapping catheter is removed from the guide sheath 504, the physician introduces the RF ablation catheter 100 through the guide sheath 504 and into the heart 500. Once the catheter distal region 102 is located within the heart 500, the physician can inflate the electrode body 120 by introducing under pressure the inflation medium 126 through the inflation port 134 (FIG. 1) located on the handle 133.

The physician can then image, e.g., ultrasonically, the interior of the heart 500, including the targeted tissue ablation site 502, which would preferably appear on a display unit (not shown) of the signal processor 400 (FIG. 1) as a 360-degree two-dimensional image of the heart. While viewing the image on the display unit, the physician can identify anatomical landmarks within the heart 500, and manipulate the catheter 100 until the catheter distal region 102 is adjacent the targeted tissue ablation site 502. The physician can operate the collar 190 on the handle assembly 132 (FIG. 1) to aid in placing the catheter distal region 102 infirm contact with the targeted tissue ablation site 502.

Once the catheter distal region 102 is in contact with the targeted tissue ablation site 502, the physician operates the RF generator 200 to transmit RF energy from the electrode body 120 into the targeted tissue ablation site 502 to create a lesion 506 with the desired characteristics.

Once the ablation process is completed, the physician can then deflate the electrode body 120 by removing the inflation medium 126 out through the inflation port 134. The physician can then remove the catheter 100 and guide sheath 504 from the patient's vasculature.

While preferred methods and embodiments have been shown and described, it will be apparent to one of ordinary skill in the art that numerous alterations may be made without departing from the spirit or scope of the invention. Therefore, the invention is not to be limited except in accordance with the following claims.

We claim:

1. An electrode assembly adapted to transmit electrical energy for ablating body tissue, comprising:
   an expandable and collapsible non-compliant body made of a durable material and defining an interior adapted to receive a medium containing ions, the body including a porous region;
   an electrode adapted to transmit electrical energy located in the interior of the body;
   a microporous membrane located on the porous region of the non-compliant body, the microporous membrane sized to pass ions contained in the medium without substantial medium perfusion therethrough, to thereby enable ionic transport of electrical energy from the ion-containing medium to the exterior of the electrode assembly to ablate body tissue.

2. The electrode assembly of claim 1, wherein the non-compliant body is made of a material from the group consisting of Nylon, PET, PeBax, IEBA and any of the polymers used in making an angioplasty balloon.

3. The electrode assembly of claim 1, wherein the non-compliant body is an angioplasty balloon.

4. The electrode assembly of claim 1, wherein the membrane is made of a material from the group consisting of regenerated cellulose, nylon, nylon 6, nylon 6/6, polycarbonate, poly(vinylidene fluoride), a poly(vinylidene fluoride) and poly(NSD-vinylpyrrolidone) combination, polyethersulfone, modified acylic copolymers, and cellulose acetate.

5. The electrode assembly of claim 1, wherein the porous region of the non-compliant body includes pores having a pore size in the range of 5 to 1,000 microns.

6. The electrode assembly of claim 1, wherein the microporous membrane includes pores having a pore size in the range of 0.001 to 0.100 microns.

7. The electrode assembly of claim 1, wherein the non-compliant body includes an exterior surface and the microporous membrane is located on the exterior surface of the body.

8. The electrode assembly of claim 1, wherein the non-compliant body includes an interior surface and the microporous membrane is located on the interior surface of the body.

9. An electrode assembly adapted to transmit electrical energy for ablating body tissue, comprising:
   an expandable and collapsible non-compliant body made of a durable material and defining an interior adapted to receive a medium containing ions, the body including a porous region having a plurality of pores;
   an electrode adapted to transmit electrical energy located in the interior of the body;
   a microporous coating located on the porous region of the non-compliant body and including microporous plugs located in the pores of said porous region, the microporous coating sized to pass ions contained in the medium without substantial medium perfusion therethrough, to thereby enable ionic transport of electrical energy from the ion-containing medium to the exterior of the electrode assembly to ablate body tissue.

10. The electrode assembly of claim 9, wherein the non-compliant body is made of a material from the group consisting of Nylon, PET, PeBax, IEBA and any of the polymers used in making an angioplasty balloon.

11. The electrode assembly of claim 9, wherein the non-compliant body is an angioplasty balloon.

12. The electrode assembly of claim 9, wherein the coating is made of a material from the group consisting of regenerated cellulose, nylon, nylon 6, nylon 6/6, polycarbonate, poly(vinylidene fluoride), a poly(vinylidene fluoride) and poly(N-vinylpyrrolidone) combination, polyethersulfone, modified acylic copolymers, and cellulose acetate.

13. The electrode assembly of claim 9, wherein the pores of the porous region of the non-compliant body have a pore size in the range of 5 to 100 microns.

14. The electrode assembly of claim 9, wherein the microporous coating includes pores having a pore size in the range of 0.001 to 0.100 microns.

15. An electrode assembly adapted to transmit electrical energy for ablating body tissue, comprising:
   an expandable and collapsible electrode body including a pair of non-compliant body ends and a microporous intermediate section joining the ends, the ends and intermediate section defining
   an interior adapted to receive a medium containing ions,
   an electrode adapted to transmit electrical energy located in the interior of the body, and
   the microporous intermediate section sized to pass ions contained in the medium without substantial medium perfusion therethrough, to thereby enable ionic transport of electrical energy from the ion-containing medium to the exterior of the electrode assembly to ablate body tissue;
   wherein the non-compliant body ends are angioplasty balloon ends.

16. An electrode assembly adapted to transmit electrical energy for ablating body tissue, comprising:
   an expandable and collapsible electrode body including a pair of non-compliant body ends and a microporous intermediate section joining the ends, the ends and intermediate section defining an interior adapted to receive a medium containing ions,
   an electrode adapted to transmit electrical energy located in the interior of the body, and
   the microporous intermediate section sized to pass ions contained in the medium without substantial medium perfusion therethrough, to thereby enable ionic transport of electrical energy from the ion-containing medium to the exterior of the electrode assembly to ablate body tissue;
   wherein the body ends are substantially funnel-shaped and the microporous intermediate section is substantially tubular.

17. An electrode assembly adapted to transmit electrical energy for ablating body tissue, comprising:
   an expandable and collapsible non-compliant body made of a durable material and defining an interior adapted to receive a medium containing ions, the body having a step-shaped configuration formed by a first-diameter portion and a second-diameter portion with a diameter greater than the first-diameter portion;
   an electrode adapted to transmit electrical energy located in the interior of the body;
   a microporous structure located in the first-diameter portion of the non-compliant body, the microporous structure sized to pass ions contained in the medium without substantial medium perfusion therethrough, to thereby enable ionic transport of electrical energy from the ion-containing medium to the exterior of the electrode assembly to ablate body tissue.

18. The electrode assembly of claim 17, wherein the first diameter portion of the body includes a porous region and the microporous structure includes a microporous membrane adhered to the porous region of the body.

19. The electrode assembly of claim 18, wherein the body includes an inside surface and the microporous membrane is adhered to the inside surface of the body.

20. The electrode assembly of claim 18, wherein the body includes an outside surface and the microporous membrane is adhered to the outside surface of the body.

21. The electrode assembly of claim 17, wherein the first diameter portion of the body includes a porous region having a plurality of pores and the microporous structure includes a microporous coating adhered to the porous region of the body, the microporous coating including microporous plugs located in the pores of said porous region of the body.

* * * * *